(12) United States Patent
Lee (10) Patent No.: US 10,610,686 B2
(45) Date of Patent: Apr. 7, 2020

(54) ELECTRICAL BRAIN STIMULATION SYSTEM

(71) Applicant: YBRAIN INC., Seoul (KR)

(72) Inventor: Kiwon Lee, Seoul (KR)

(73) Assignee: YBRAIN INC., Seoul (KR)

( * ) Notice: Subject to any disclaimer, the term of this patent is extended or adjusted under 35 U.S.C. 154(b) by 76 days.

(21) Appl. No.: 14/285,822

(22) Filed: May 23, 2014

(65) Prior Publication Data

US 2015/0224311 A1 Aug. 13, 2015

Related U.S. Application Data

(60) Provisional application No. 61/937,113, filed on Feb. 7, 2014.

(51) Int. Cl.
*A61N 1/36* (2006.01)
*A61N 1/08* (2006.01)
*A61N 1/05* (2006.01)
*A61N 1/04* (2006.01)

(52) U.S. Cl.
CPC ........... *A61N 1/36025* (2013.01); *A61N 1/08* (2013.01); *A61N 1/36014* (2013.01); *A61N 1/0456* (2013.01); *A61N 1/0526* (2013.01); *A61N 2001/083* (2013.01)

(58) Field of Classification Search
CPC ........... A61B 5/04001; A61B 5/04085; A61B 5/04087; A61B 5/04282; A61B 5/14552; A61B 5/4836; A61B 5/6832; A61B 8/0808; A61N 1/32; A61N 1/0472; A61N 1/36146; A61N 1/36125; A61N 1/36139; A61N 1/36153; A61N 1/0492; A61N 1/0456; A61N 1/0476; A61N 1/08; A61N 1/36014; A61N 1/3937; A61N 1/0408; A61N 1/0526; A61N 1/0529; A61N 1/0534; A61N 1/303; A61N 2001/083; A61H 2201/165; A61H 2201/5071
See application file for complete search history.

(56) References Cited

U.S. PATENT DOCUMENTS 8,311,639 B2 * 11/2012 Parker .................. A61N 1/0551
607/62
2010/0204766 A1 * 8/2010 Zdeblick .............. A61B 5/0422
607/119
2011/0288610 A1 11/2011 Brocke
2012/0296390 A1 11/2012 Nakashima et al.
2013/0079659 A1 3/2013 Akhadov et al.

FOREIGN PATENT DOCUMENTS

| JP | 2010516329 A | 5/2010 |
| JP | 2012520730 A | 9/2012 |
| JP | 2012239696 A | 12/2012 |
| JP | 2013507174 A | 3/2013 |
| KR | 1020030002677 | 1/2003 |
| KR | 1020100014815 | 2/2010 |
| KR | 101094350 | 12/2011 |

* cited by examiner

*Primary Examiner* — Deborah L Malamud
(74) *Attorney, Agent, or Firm* — Studebaker & Brackett PC (57) ABSTRACT

An electrical brain stimulation system includes at least two electrodes configured to be adhered to a subject, a power supply configured to supply electric power to the electrodes, and a control unit configured to control the electric power to be supplied to the electrodes by limiting at least one of a variation and a maximum of energy of the electric power.

6 Claims, 11 Drawing Sheets

Fig. 11

ELECTRICAL BRAIN STIMULATION SYSTEM

CROSS-REFERENCE TO RELATED APPLICATION

This application claims the priority of the U.S. Provisional Application No. 61/937,113 filed on Feb. 6, 2014 in the U.S. Patent and Trademark Office, and all the benefits accruing therefrom under 35 U.S.C. § 119. The contents of the above-listed provisional application in their entirety are herein incorporated by reference.

TECHNICAL FIELD

The present disclosure relates to an electrical brain stimulation system.

Recently, an electrical brain stimulation to central nerves in the brain is widely practiced to find an area where epilepsy recursively occurs or, during a surgery, gain functional guidance for certain areas of the brain such as a psychomotor area and a language area.

For an example, tDCS (transcranial direct current stimulation) is known to have effect on treatment for depression, Parkinson's disease, functional impairment following stroke, epilepsy, chronic neuropathic pain, etc.

Electric brain stimulation activates or suppresses connection between nerves, thus having effect on improving symptoms.

SUMMARY

In accordance with some embodiments, there is provided an electrical brain stimulation system, the system comprising at least two electrodes configured to be adhered to a subject, a power supply configured to supply electric power to the electrodes, and a control unit configured to control the electric power to be supplied to the electrodes by limiting at least one of a variation and a maximum of energy of the electric power.

In accordance with some embodiments, there is provided an electrical brain stimulation system, the system comprising at least two electrodes configured to be adhered to a subject, a power supply configured to supply electric power to the electrodes, and a control unit configured to control the electric power to be supplied to the electrodes, based on an impedance variation of the electrodes, to limit at least one of an energy variation and an energy maximum of the electric power to be supplied to the electrodes adhered to the subject.

In accordance with some embodiments, there is provided a method of brain stimulation, performed by an electrical brain stimulation system, the method comprising adhering at least two electrodes to a subject, supplying electric power to the electrodes, and controlling the electric power to be supplied to the electrodes by limiting at least one of a variation and a maximum of energy of the electric power, when at least a first part of at least one of the electrodes is not adhered to the subject, and second parts of the electrodes are adhered to the subject to supply the electric power to the subject.

DETAILED DESCRIPTION

An electrical brain stimulation system will be described more fully hereinafter with reference to the accompanying drawings, in which some embodiments are shown. Advantages and features of some embodiments accomplishing the same are hereafter detailed with reference to the accompanying drawings. The electrical brain stimulation system is embodied in different forms and should not be construed as limited to the embodiments set forth herein. Rather, these embodiments are provided so that this disclosure will be thorough and complete, and will fully convey the scope of the electrical brain stimulation system to those skilled in the art. The same reference numbers indicate the same component throughout the specification.

Unless defined otherwise, all technical and scientific terms used herein have the same meaning as commonly understood by one of ordinary skill in the art to which this application belongs. It is noted that the use of any and all examples, or exemplary terms provided herein is intended merely to better illuminate the electrical brain stimulation system and is not a limitation on the scope of the electrical brain stimulation system unless otherwise specified. Further, unless defined otherwise, all terms defined in generally used dictionaries may not be overly interpreted.

The use of the terms "a" and "an" and "the" and similar referents in the context of describing the electrical brain stimulation system (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

A detailed description of the electrical brain stimulation system is hereafter presented with reference to the accompanying drawings.

In some embodiments, the same marks are used for components having the same composition, and those components are explained in an embodiment for another embodiments, only components different from those of the described embodiment(s) are explained.

Also, electrodes, being a component of the electrical brain stimulation system, are described to be adhered to a scalp, but are not limited. The electrodes can be adhered to skin besides subject's scalp.

Figure 1:
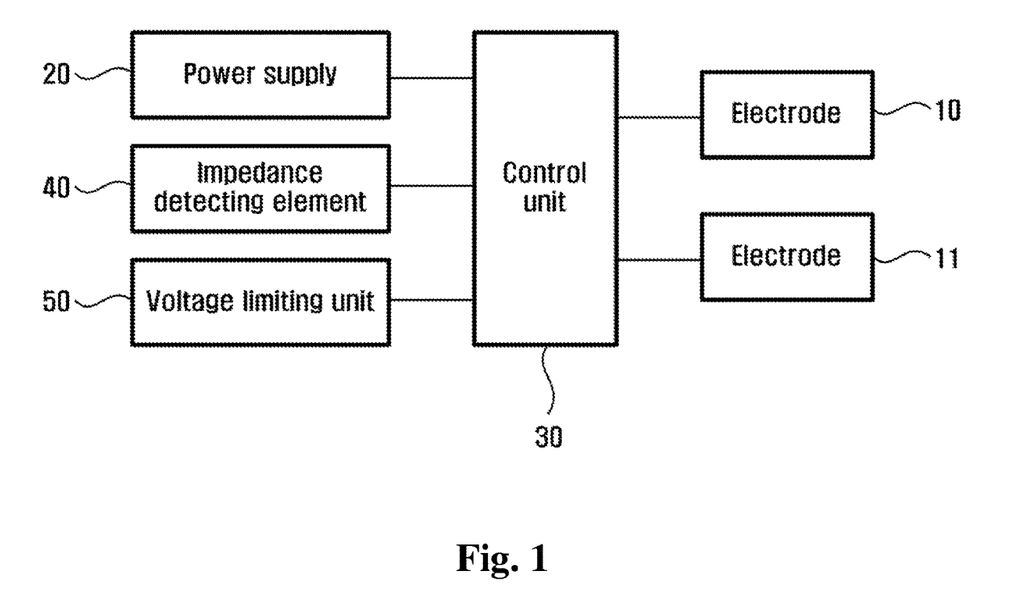
FIG. 1 is a schematic block diagram of an electrical brain stimulation system according to some embodiments.
Figure 2:
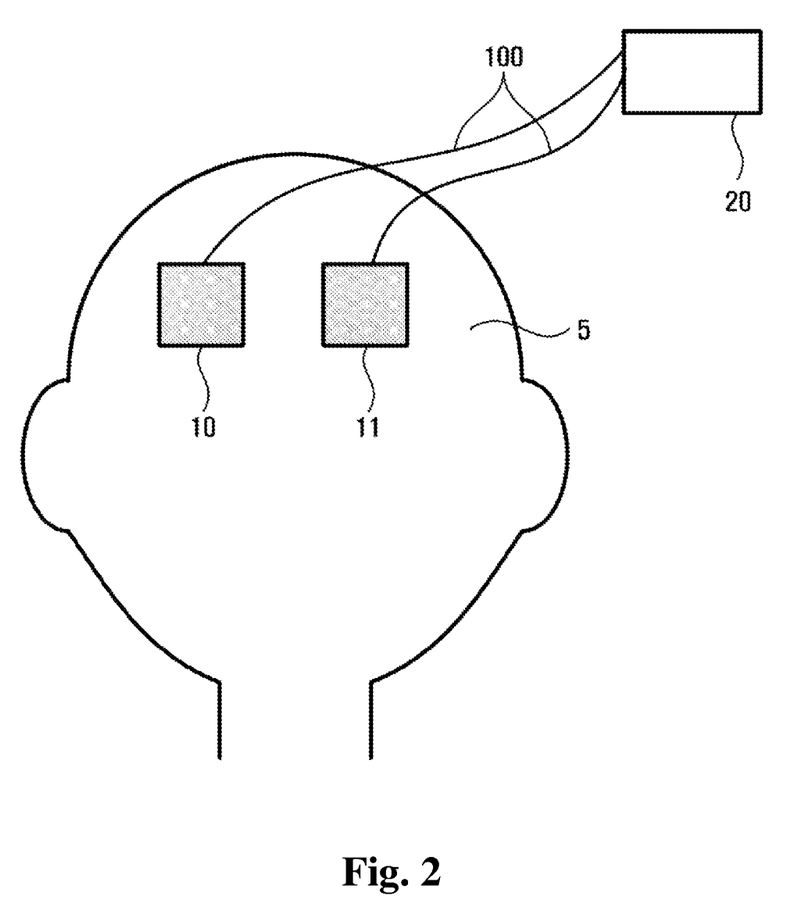
FIG. 2 is a schematic drawing that shows electrodes are properly adhered to a subject.
Figure 3:
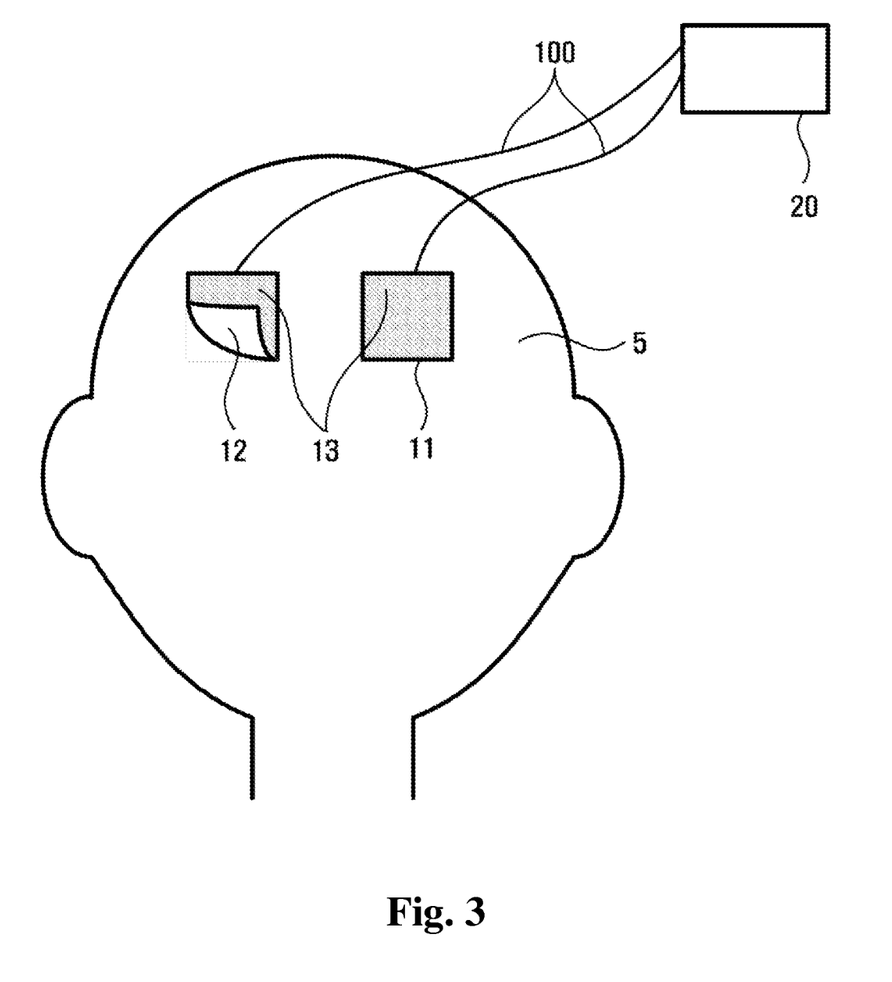
FIG. 3 is a schematic drawing that shows at least a first part of electrodes is not adhered to a subject.

FIG. 1 is a schematic block diagram of an electrical brain stimulation system according to some embodiments, FIG. 2 is a schematic drawing that shows electrodes are properly adhered to a subject, and FIG. 3 is a schematic drawing that shows at least a first part of electrodes is not adhered to the subject.

As shown in FIG. 1, an electrical brain stimulation system in some embodiments includes electrodes 10 and 11, a power supply 20, a control unit 30, and an impedance detecting element 40.

The electrodes 10 and 11 are comprised of flexible and conductive material, and are detachable from a subject's scalp 5. The electrodes 10 and 11 have one cross section shape of the following: a quadrangle, a circle, an oval, or a polygon. The electrodes 10 and 11 are elastically or visco-elastically transformed so as to be easily adhered to the subject.

The control unit 30, in some embodiments, includes one or more physical, actual storage devices. Examples of physical, actual storage devices include, but are not limited to, magnetic media such as, a hard disk, a floppy disk, and a magnetic tape, optical media such as a CD-ROM and a DVD, magneto-optical media such as a floptical disk, and a hardware device configured especially to store and execute a program, such as a ROM, a RAM, a solid state drive, and a flash memory. The control unit 30 is implemented, in some embodiments, by one or more programmed processors and/or application-specific integrated circuits (ASICs).

As shown in FIG. 2, a power supply 20 is electrically connected with electrodes 10 via a cable 100, to supply electric power to electrodes 10 and 11. The electrodes 10 and 11 contact with the scalp of the subject, and for each electrode the cable 100 is connected with the power supply 20.

As shown in FIG. 3, a control unit 30, when a first part 12 of the electrode 10 is not adhered to the scalp 5 of the subject, and second parts 13 of electrodes 10 and 11 is adhered to the scalp 5 of the subject, controls the electric power to be supplied to the electrodes 10 and 11 so that the sum of energy supplied to the second parts 13 of the electrodes 10 and 11 are decreased. In the embodiments of FIG. 3, the whole of the electrode 11 is also a second part 13, because the whole of the electrode 11 is adhered to the scalp 5 of the subject.

Hereinafter, for electrodes 10 and 11 to be adhered to the scalp 5, a first part is an area of the electrodes 10 and 11, not adhered to the scalp 5 of the subject, due to bad adherence, and a second part is an area of the electrodes 10 and 11, adhered to the scalp 5 of the subject.

An impedance detecting element 40 measures an impedance value at the electrodes 10 and 11, and frequently sends one or more variations of the impedance values to the control unit 30.

Furthermore, an electrical brain stimulation system according to some embodiments includes a voltage limiting unit 50 that limits a voltage of an electric power to be supplied to the second parts of the electrodes 10 and 11.

Detailed operating of the electrical brain stimulation system by the aforementioned composition according to the above embodiments is presented as the following.

As shown in FIG. 2, in some embodiments, electrodes 10 and 11 are well adhered to the scalp 5 of the subject to supply electric power to the brain of the subject. Differently, as shown in FIG. 3, in some embodiments, electrodes 10 and 11 are not well adhered to the scalp 5 such that a part of the electrode 10 is detached by an external force, while electrical brain stimulation is being processed by parts of the electrodes 10 and 11, adhered to the scalp of the subject. In FIG. 3, a first part 12 of the electrode 10 is not adhered to the subject and second parts 13 of the electrodes 10 and 11 are adhered to the subject. In this case, impedance measured by the impedance detecting element 40 is sharply increased, and the voltage at the second parts 13 of the electrodes 10 and 11 is sharply increases, thus the sum of energy at the second parts 13 of the electrodes 10 and 11 is excessively increased.

In some embodiments, when at least a part of at least one electrode of the electrodes 10 and 11 is not well adhered to the scalp 5 of a subject, the control unit 30, based on a variation of impedance values of the electrodes 10 and 11 measured by an impedance detecting element 40, controls at least one of a magnitude and a rate of change of a voltage of the electrical power to be supplied to the second parts 13 of the electrodes 10 and 11 by a voltage limiting unit 50 with a guidance of a rate of energy increase and a maximum energy predetermined so that the sum of energy to be supplied to the second parts 13 of the electrodes 10 and 11 does not excessively increase more than a percentage of a certain amount. Herein, it is possible for the second parts 13 of the electrodes 10 and 11 to be supplied gradually increasing voltage so that intense stimulation by sudden energy increase to the subject does not occur, to improve adherence of the electrodes 10 and 11 by the subject's recognition before the sum of energy reach the limit, and to terminate the stimulation automatically when the sum of energy reaches the predetermined limit.

Thus, even if at least a part of at least one electrode of the electrodes 10 and 11 is not well adhered to the scalp 5 of a subject by an external force, since the sum energy of the second parts 13 of the electrodes 10 and 11, adhered to the subject, is prevented from abnormally increasing. An electrical brain stimulation is safely performed.

Figure 4:
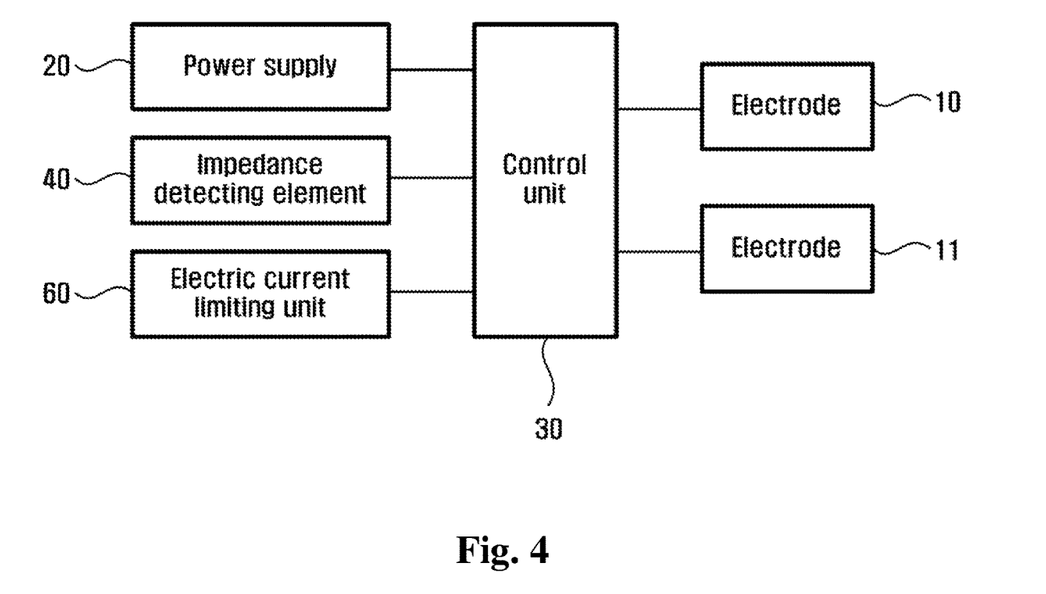
FIG. 4 is a schematic block diagram of an electrical brain stimulation system according to some embodiments.

FIG. 4 is a schematic block diagram of an electrical brain stimulation system according to some embodiments. The electrical brain stimulation system according to some embodiments, different from the abovementioned embodiments of FIG. 1, includes an electric current limiting unit 60.

An electric current limiting unit 60 limits an electric current of electric power to be supplied to electrodes 10 and 11, adhered to the scalp 5 of a subject.

In an electrical brain stimulation system according to some embodiments, if at least a first part of at least one of the electrodes 10 and 11 is not well adhered to the scalp 5 of the subject, a control unit 30, based on a variation of impedance values of the electrodes 10 and 11 measured by an impedance detecting element 40, controls at least one of a magnitude and a rate of change of the electric current of an electrical power to be supplied to the second parts 13 of the electrodes 10 and 11 by the electric current limiting unit 60 with a guidance of a rate of energy increase and the a maximum energy predetermined so that the sum of energy to be supplied to the second parts 13 of the electrodes 10 and 11 does not excessively increase more than a percentage of a certain amount, thus abnormal increase of maximum energy at the second parts 13 of the electrodes 10 and 11, adhered to the scalp 5 of a subject, is prevented. An electrical brain stimulation is safely performed, where it is possible for the second parts 13 of the electrodes 10 and 11 to supply the same magnitude of gradually increasing tidal electric current.

Figure 5:
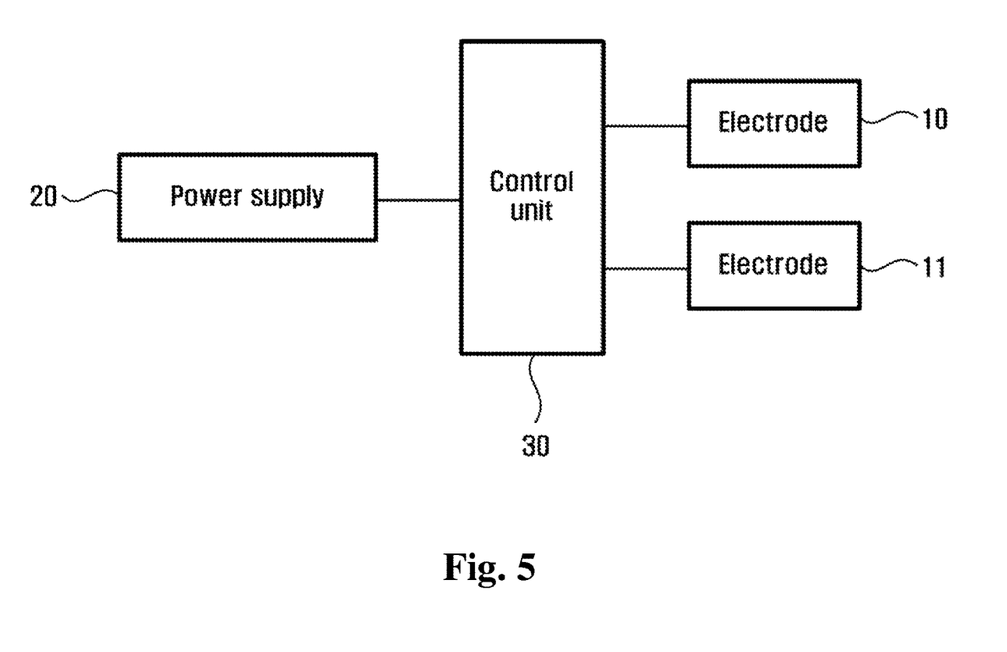
FIG. 5 is a schematic block diagram of an electrical brain stimulation system according to some embodiments.
Figure 6:
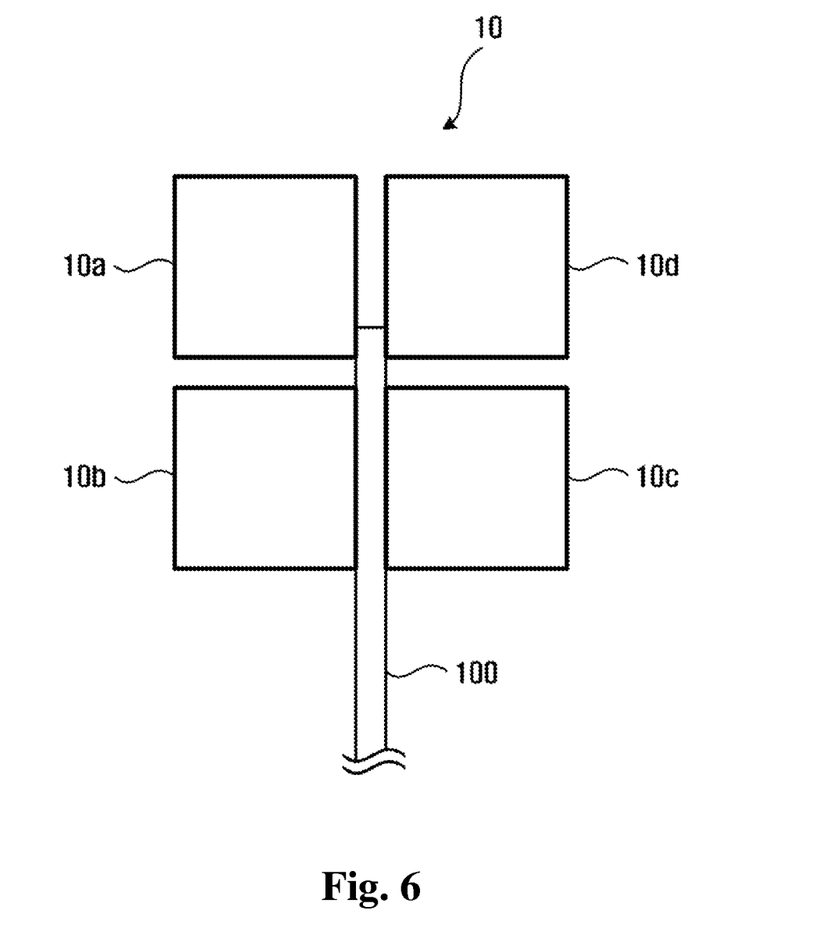
FIG. 6 is a schematic top view of an electrical brain stimulation system according to some embodiments.

FIG. 5 is a schematic block diagram of an electric brain stimulation system according to some embodiments, and FIG. 6 is a schematic top view of an electrical brain stimulation system according to some embodiments. The electric brain stimulation system according to some embodiments, different from the abovementioned embodiments of FIGS. 1 and 4, as shown in FIG. 6, an electrode 10 comprises a plurality of independent and separated unit electrodes 10a, 10b, 10c and 10d. In the embodiments, an electrode 10 is presented as a square cross section shape, but is not limited to.

Each unit electrode 10a, 10b, 10c and 10d contains an electric current limiting circuit connected to each one, and is connected to a power supply 20 by cables 100, thus electric power is individually supplied to each one from the power supply 20 via cables 100. Electric current values flowing into each unit electrode 10a, 10b, 10c and 10d are determined by an electric current limiting circuit. In some embodiments, the electric current limiting circuit is at least one of a diode or resistor. The area of each unit electrode and allowable current of the electric current limiting circuit are proportional to each other. Each current density flowing into each unit electrode is the same, and the sum of all electric currents is the same with the electric current at one electrode 10.

From this composition, for example, three unit electrodes 10a, 10b and 10c among four unit electrodes 10a, 10b, 10c and 10d are detached from the scalp 5 of a subject, the remaining one unit electrode 10d, regardless of operation of a control unit 30, supplies energy limited by an electric current limiting circuit of the remaining unit electrode 10d, to the scalp 5.

Thus, even if at least a part of one electrode of electrodes 10 and 11 is not well adhered to the scalp 5 of a subject by an external force, since the sum of energy of the unit electrodes 10a, 10b, 10c and 10d, adhered to the scalp 5 of the subject, is prevented from abnormally increasing, electrical brain stimulation is safely performed.

In some embodiments, an electrode 10 is divided into more or less than four parts. An electrode 10 comprises independent and separated n-unit electrodes, and the sum of electric current flowing into each unit electrode is equal to the electric current of one electrode 10.

Figure 7:
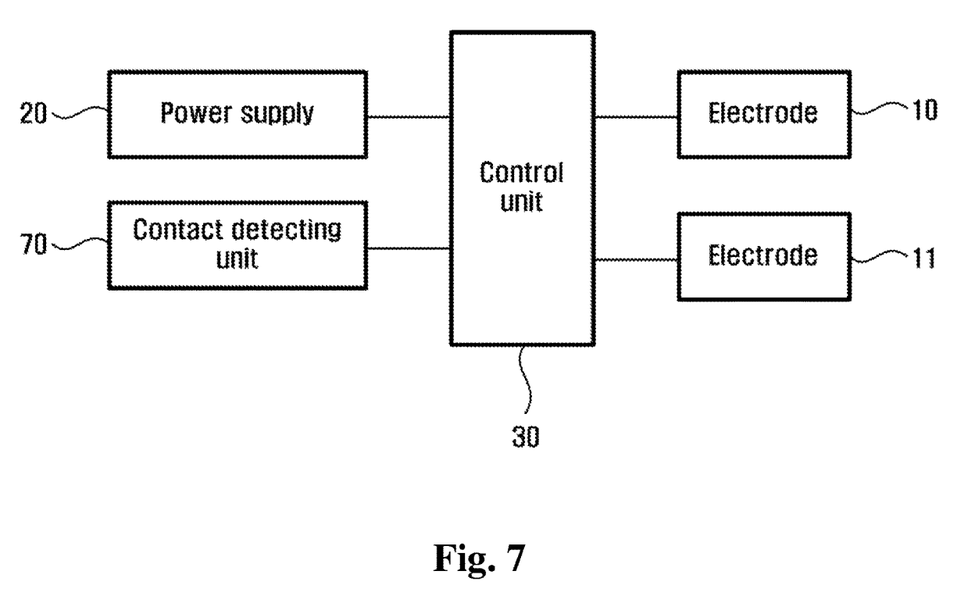
FIG. 7 is a schematic block diagram of an electrical brain stimulation system according to some embodiments.

FIG. 7 is a schematic block diagram of an electric brain stimulation system according to some embodiments. The electric brain stimulation system according to the embodiments of FIG. 7, different from the aforementioned embodiments of FIGS. 1, 4 and 5, includes a contact detection unit 70 that detects contact between electrodes 10 and 11, and the scalp 5 of a subject. In some embodiments, the contact detection unit 70 is arranged with the electrodes in one side of the electric brain stimulation. That is, the contact detection unit 70 and the electrodes 10 and 11 are arranged in one side. In some embodiments, the contact detection unit 70 and the electrodes 10 are separately arranged, not arranged in one side. Meanwhile, a plurality of contact detection units is used so as to detect bad adherence of electrodes 10 and 11.

In some embodiments, a contact detection unit 70 comprises one of the following: a capacitive touch sensor, a proximity sensor, a pressure sensor, an optical sensor, an acoustic wave sensor, a spring-loaded pin, a switch, an ambient light sensor or a light sensor.

For example embodiments, when a contact detection unit 70 is either a capacitive touch sensor or a proximity sensor, if at least a part of one electrode of electrodes 10 and 11 is not well adhered to the scalp 5 of a subject, and if it is detected that the part and the scalp 5 of the subject is not in contact with each other, a control unit 30 blocks electric power to be supplied to the electrodes 10 and 11 in accordance with the signal detected by the contact detection unit 70. Thus, abnormal increase of a maximum energy at the second parts 13 of the electrodes 10 and 11 is prevented.

For another example embodiments, when the contact detection unit 70 is a pressure sensor that detects pressure on electrodes 10 and 11, if the pressure measured by the contact detection unit 70 is above a predetermined pressure, a control unit 30 regards the electrodes 10 and 11 as normally adhered to the scalp 5 of a subject, and thus, the control unit 30 controls to keep supplying electric power to the electrodes 10 and 11.

In other example embodiments, if at least a part of one electrode of electrodes 10 and 11 is not well adhered to the scalp 5 of a subject, and if the pressure measured by the contact detection unit 70 is below a predetermined pressure, the control unit 30, in accordance with the signal of pressure measured by the contact detection unit 70, controls to block electric power to be supplied to electrodes 10 and 11. Thus, abnormal increase of a maximum energy at the second parts 13 of the electrodes 10 and 11 is prevented, wherein the pressure sensor is either a sensor detecting pressure or a pressure switch pressed above a predetermined pressure.

For another example embodiments, when the contact detection unit 70 is a light sensor detecting light between electrodes 10 and 11, and a subject, if light is not detected by the contact detection unit 70 between the electrodes 10 and 11, and the scalp 5 of the subject, the control unit 30 regards the electrodes 10 and 11 as normally adhered to the scalp 5 of a subject. The control unit 30 controls to supply electric power to the electrodes 10 and 11.

In other example embodiments, if at least a part of at least one electrode of electrodes 10 and 11 is not well adhered to the scalp 5 of a subject, and if light is detected by the contact detection unit 70 between at least one electrode of the electrodes 10 and 11, and the scalp 5 of a subject, the control unit 30, in accordance with the signal of pressure measured by the contact detection unit 70, controls to block electric power to be supplied to electrodes 10 and 11. The control unit 30 prevents abnormal increase of a maximum energy at the second parts 13 of the electrodes 10 and 11, wherein the light detected by the contact detection unit 70 is either natural light or light generated from another area of the electrodes 10.

Figure 8:
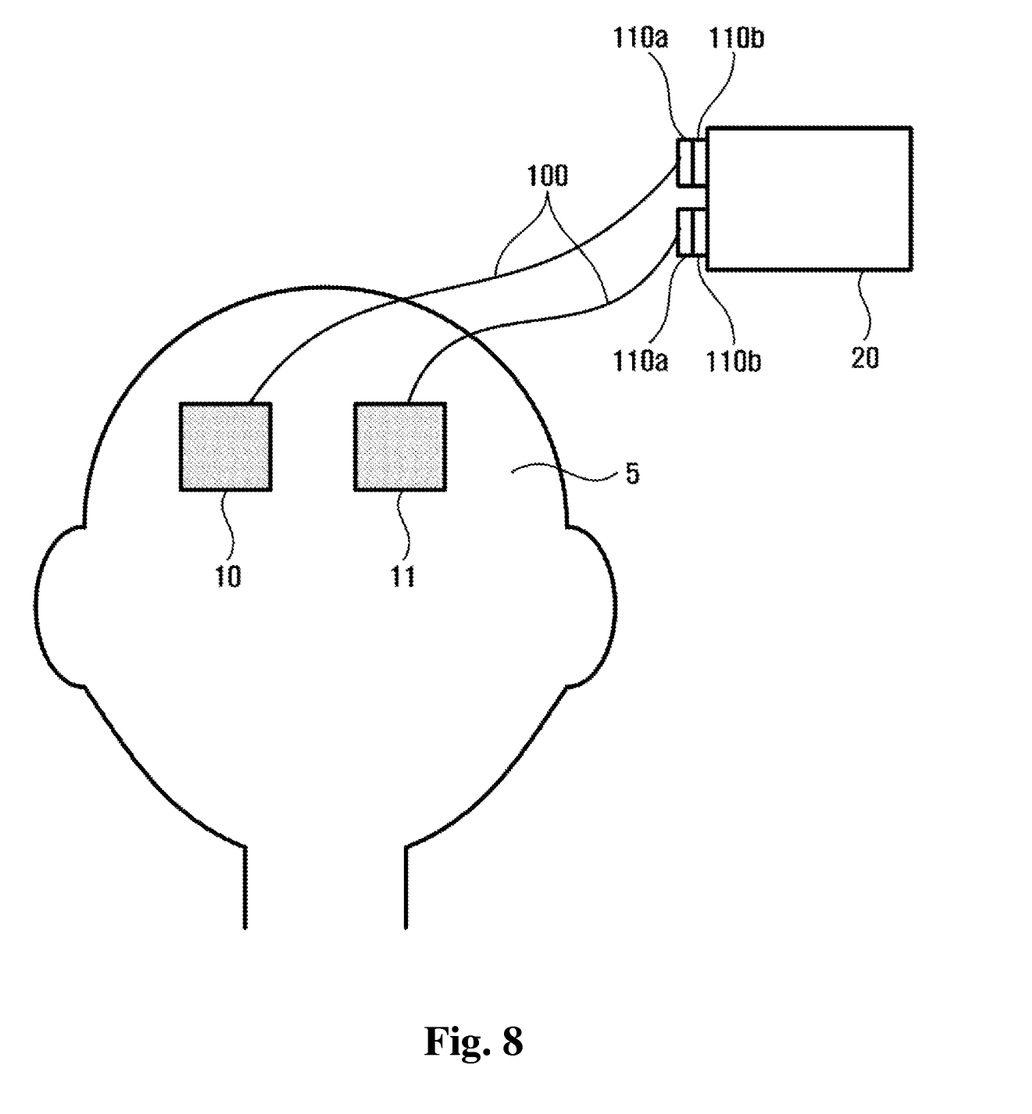
FIGS. 8 and 9 are schematic drawings that show electrodes are connected and disconnected by a magnetic connector.
Figure 9:
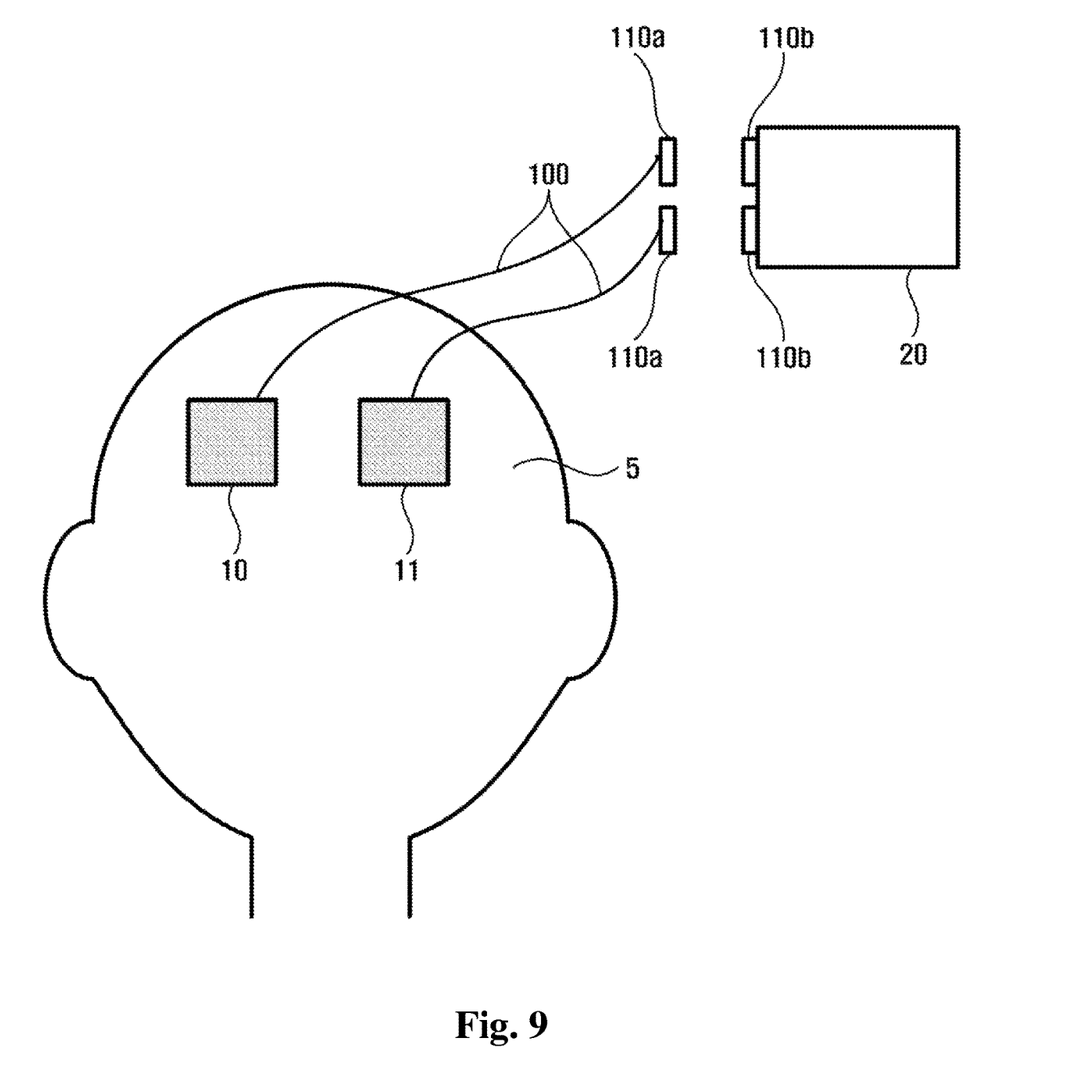

FIGS. 8 and 9 are schematic drawings that show electrodes are connected and disconnected by a magnetic connector.

In the meantime, in some embodiments of the electrical brain stimulation system, one part of cables 100 that electrically connect electrodes 10 and 11 and a power supply 20 so that external forces is not passed on electrodes 10 and 11 and a power supply 20 is connected by a magnetic connector 110a and 110b fixed by a magnet, or the cables 100 are disconnected from the electrodes 10 and 11 or the power supply 20. Thus, it is possible to abnormal increase of a maximum energy of the electrodes 10 and 11 adhered to the scalp of the subject 5 when the electrodes 10 and 11 have bad adherence to the scalp of a subject 5 due to an external force. An electrical brain stimulation is safely performed.

Figure 10:
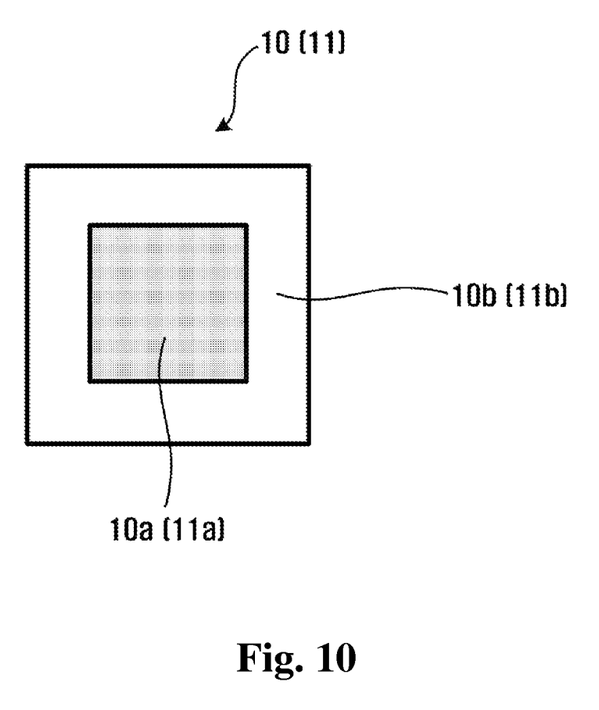
FIG. 10 is a schematic drawing that shows electrodes comprise a conductive portion and a non-conductive portion.

FIG. 10 is a schematic drawing that shows electrodes comprise a conductive portion and a non-conductive portion.

Furthermore, in some embodiments of the electrical brain stimulation system, electrodes of the electrical brain stimulation system include a first portion 10a and 11a which is more likely to be adhered to a subject 5. In some embodiments, the first portion 10a and 11a is a central portion of the electrodes 10 and 11. The first portion 10a and 11a is comprised of conductive material and has conductivity. Meanwhile, the electrodes 10 and 11 include a second portion 10b and 11b which is less likely to be adhered to the subject 5. In some embodiments, the second portion 10b and 11b is the rim of the electrodes 10 and 11. The second portion 10b and 11b is comprised of nonconductive material and has non-conductivity. Thus, energy density of second parts, which are adhered to the subject, is uniform even if a first part is detached during an electrical brain stimulation. Further, a maximum energy of the electrodes 10 and 11 is prevented from abnormally increasing. An electrical brain stimulation is safely performed.

In aforementioned embodiments, the impedance detecting element 40 is contained in the electrical brain stimulation system, but the embodiments are not limited to. A voltage detecting element and an electric current detecting element are contained instead of the impedance detecting element to measure impedance.

Figure 11:
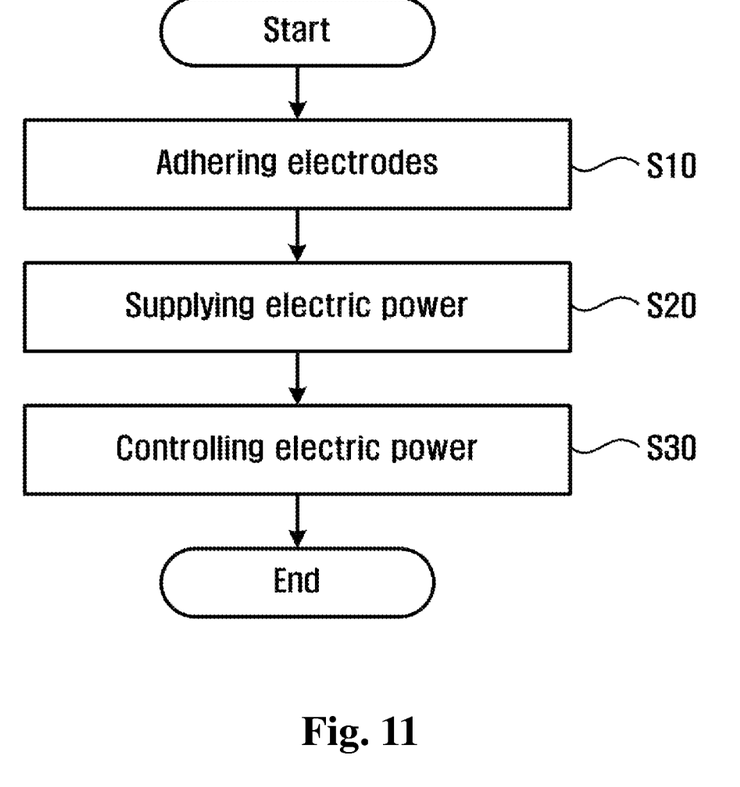
FIG. 11 is a flow chart of a method of brain stimulation according to some embodiments.

FIG. 11 is a flow chart of a method of brain stimulation according to some embodiments.

The method of brain stimulation according to some embodiments comprises the steps of: adhering at least two electrodes to a subject (S10); supplying electric power to the electrodes (S20); and controlling the electric power to be supplied to the electrodes by limiting at least one of a variation and a maximum of energy of the electric power, when at least a first part of at least one of the electrodes is not adhered to the subject, and second parts of the electrodes are adhered to the subject to supply the electric power to the subject (S30).

In concluding the detailed description, those skilled in the art will appreciate that many variations and modifications can be made to the preferred embodiments without substantially departing from the principles of the some embodiments described above. Therefore, the described some embodiments are used in a generic and descriptive sense only and not for purposes of limitation.

I claim:

1. An electrical brain stimulation system, the system comprising:
   at least two electrodes configured to be adhered to a subject to supply electric currents to the subject,
      wherein the each of the electrodes has a single layer and a single unibody structure including a center portion and an outer portion surrounding the center portion, the center portion is comprised of conductive material and has conductivity, and the outer portion is comprised of nonconductive material and has non-conductivity;
   a power supply configured to supply electric power to the electrodes;
   a contact detection unit arranged adjacent to the electrodes, and configured to determine whether at least a first part of at least one of the electrodes is not adhered to the subject, based on a determination whether a characteristic of a contact between each unit electrode and the subject meets a predetermined criterion,
      wherein the characteristic of the contact is determined by a touch sensor included in the contact detection unit, and
      wherein the first part that is not adhered to the subject is a corner portion of the single layer and the single unibody structure and is not adhered by being bent from the second parts adhered to the subject; and
   a control unit configured to control, when the first part of at least one of the electrodes is not adhered to the subject, the electric power supplied to second parts of the electrodes adhered to the subject, by limiting a maximum of energy of the electric power,
   wherein each of the electrodes comprises a plurality of separated unit electrodes each having an electric current limiting circuit configured to control an electric current flowing into the corresponding unit electrode.

2. The system of claim 1, wherein a current density flowing into each unit electrode is the same.

3. The system of claim 1, further comprising:
   a voltage limiting unit configured to limit a voltage of the electric power to be supplied to each unit electrode.

4. The system of claim 3, wherein the voltage limiting unit is further configured to limit at least one of a magnitude and a rate of change of the voltage of the electric power to be supplied to each unit electrode, based on an impedance variation of a first unit electrode.

5. The system of claim 1, wherein the control unit is further configured to control, when the contact detection unit determines that the first part is not adhered to the subject, the electric power supplied to the second parts of the electrodes adhered to the subject, by limiting a variation of energy of the electric power.

6. The system of claim 5, wherein the control unit is further configured to control, when the contact detection unit determines that the first part is not adhered to the subject, the electric power to be supplied to each unit electrodes, based on an impedance variation of the unit electrodes, to limit the energy variation of the electric power to be supplied to each unit electrodes adhered to the subject.

* * * * *